United States Patent
Hill et al.

(10) Patent No.: US 9,717,478 B2
(45) Date of Patent: Aug. 1, 2017

(54) REFINEMENT OF AN ANATOMICAL MODEL USING ULTRASOUND

(75) Inventors: Anthony D. Hill, Minneapolis, MN (US); D. Curtis Deno, Andover, MN (US); Robert D. Aiken, Stillwater, MN (US); Hua Zhong, Pittsburgh, PA (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 778 days.

(21) Appl. No.: 12/979,210

(22) Filed: Dec. 27, 2010

(65) Prior Publication Data

US 2012/0165672 A1    Jun. 28, 2012

(51) Int. Cl.
A61B 8/00 (2006.01)
A61B 8/08 (2006.01)
A61B 8/14 (2006.01)

(52) U.S. Cl.
CPC ............ *A61B 8/463* (2013.01); *A61B 8/0883* (2013.01); *A61B 8/14* (2013.01)

(58) Field of Classification Search
USPC .................................................. 600/450–451
See application file for complete search history.

(56) References Cited

U.S. PATENT DOCUMENTS

| | | | |
|---|---|---|---|
| 6,456,867 B2* | 9/2002 | Reisfeld ......................... | 600/407 |
| 6,950,689 B1* | 9/2005 | Willis et al. .................. | 600/407 |
| 7,263,397 B2 | 8/2007 | Hauck et al. | |
| 7,386,339 B2 | 6/2008 | Strommer et al. | |
| 7,670,297 B1 | 3/2010 | Hauck et al. | |
| 7,773,806 B2 | 8/2010 | Cremers et al. | |
| 2003/0038802 A1* | 2/2003 | Johnson et al. ............... | 345/420 |
| 2005/0203385 A1* | 9/2005 | Sundar et al. ................. | 600/427 |
| 2007/0049817 A1* | 3/2007 | Preiss .................. | A61B 5/0422 600/407 |
| 2008/0137927 A1* | 6/2008 | Altmann .............. | A61B 8/4488 382/131 |
| 2008/0194957 A1* | 8/2008 | Hoctor et al. ................ | 600/443 |
| 2008/0221643 A1 | 9/2008 | Olson | |
| 2009/0148012 A1* | 6/2009 | Altmann et al. .............. | 382/128 |
| 2009/0163810 A1 | 6/2009 | Kanade et al. | |
| 2010/0168557 A1 | 7/2010 | Deno et al. | |

(Continued)

FOREIGN PATENT DOCUMENTS

| WO | WO 2009/031327 | * | 3/2009 |
| WO | WO2009/060751 | * | 5/2009 |

OTHER PUBLICATIONS

International Search Report and Written Opinion, PCT/US2011/051443, Jan. 5, 2012.

(Continued)

*Primary Examiner* — Amanda Lauritzen Moher
*Assistant Examiner* — Shahdeep Mohammed
(74) *Attorney, Agent, or Firm* — Dykema Gossett PLLC

(57) ABSTRACT

A method of displaying the influence of an aspect of a model includes acquiring a two-dimensional echocardiogram having a variable intensity; relating the two-dimensional echocardiogram to a plurality of mapping points, the mapping points existing in a three-dimensional model space; determining a degree of influence value for a mapping point; and displaying the mapping point with a visual attribute that corresponds to the determined degree of influence value.

16 Claims, 13 Drawing Sheets

(56) References Cited

U.S. PATENT DOCUMENTS

2010/0168560 A1      7/2010  Hauck et al.
2010/0191111 A1*     7/2010  Azuma ......................... 600/438
2010/0256493 A1*    10/2010  Chono ......................... 600/443
2012/0155723 A1      6/2012  Deno et al.

OTHER PUBLICATIONS

Zhong, Hua, Ph.D. Thesis, "Image Guided Navigation for Minimally Invasive Surgery," Carnegie Mellon University, Sep. 24, 2007.
CartoSound System Marketing Brochure, "CartoSound Image Integration Module with SoundStar Catheter," Biosense-Webster, 2007.
AcuNav European Marketing Brochure, "AcuNav Ultrasound Catheter," Biosense-Webster, 2006.
Singh, Sheldon et al., Carto-Sound publication, "Image Integration Using Intracardiac Ultrasound to Guide Catheter Ablation of Atrial Fibrillation," Heart Rhythm, Nov. 2008; 5:1548-1555.

* cited by examiner

REFINEMENT OF AN ANATOMICAL MODEL USING ULTRASOUND

CROSS REFERENCE TO RELATED APPLICATIONS

This application is related to co-pending U.S. patent application Ser. No. 12/979,170, filed Dec. 27, 2010; the entire disclosure of which is hereby incorporated by reference as though fully set forth herein.

BACKGROUND OF THE INVENTION a. Field of the Invention

The present disclosure relates to catheter devices and systems, including devices and methods for refining an anatomical model using ultrasound.

b. Background Art

Electrophysiology (EP) catheters are used in connection with an ever-increasing number of procedures. Such catheters have been used, for example, for diagnostic, therapeutic, mapping, and ablative procedures. Catheters are commonly manipulated through a patient's vasculature to an intended site, for example a site within the patient's heart, and may carry one or more ultrasound transducers, position sensors, or electrodes for use in sensing, mapping, ablation, or diagnosis procedures.

BRIEF SUMMARY OF THE INVENTION

A method of displaying the influence of an aspect of a model includes acquiring a two-dimensional echocardiogram having a variable intensity; relating the two-dimensional echocardiogram to a plurality of mapping points, the mapping points existing in a three-dimensional model space; determining a degree of influence value for a mapping point; and displaying the mapping point with a visual attribute that corresponds to the determined degree of influence value. In an embodiment, the visual attribute may include a symbol or a color selected from a range that is intended to convey a relative influence value.

In an embodiment, determining a degree of influence value for a mapping point may include determining a confidence value for the model; removing a mapping point from the model; and calculating the change in the confidence value of the model attributable to the removed point. The confidence value for the model may be determined by identifying a boundary from the two-dimensional echocardiogram, and calculating a distance between each of a plurality of mapping points of the model and the identified boundary; and summing the respective distances.

In an embodiment, the two-dimensional echocardiogram may be acquired from an ultrasound transducer associated with a distal portion of a catheter. The system may relate the two-dimensional echocardiogram to the plurality of mapping points by receiving an indication of the position and orientation of the ultrasound transducer; and registering the two-dimensional echocardiogram within the three-dimensional model space using the position and orientation of the ultrasound transducer. Once the relationship is achieved, the system may further refine the registration using an iterative closest point registration algorithm. In an embodiment, this algorithm may provide multiple different optimal solutions from which to choose.

DETAILED DESCRIPTION OF THE INVENTION

Figure 1:
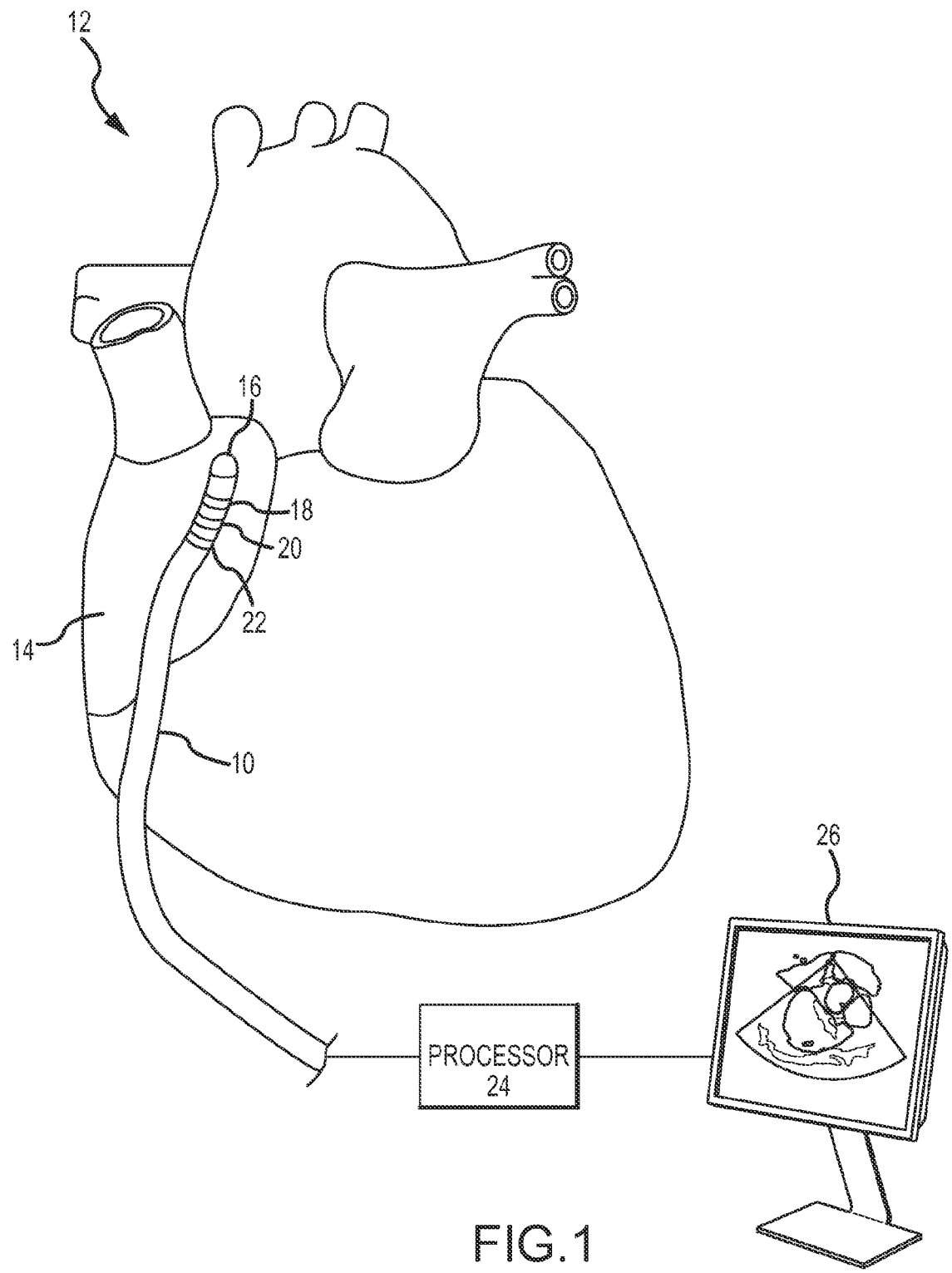
FIG. 1 is a general representation of a cardiac anatomy together with a catheter.

Referring to the drawings, wherein like reference numerals are used to identify like or identical components in the various views, FIG. 1 generally illustrates a catheter 10 positioned within a portion of a cardiac anatomy 12. As generally illustrated in FIG. 1, the catheter 10 may, for example, be positioned within the right atrium 14 of the cardiac anatomy 12. In an embodiment, the catheter 10 may be an intracardiac echo (ICE) catheter that may include one or more ultrasound transducers, such as ultrasound transducer 16. The catheter 10 may further include one or more position detectors 18, 20, 22, which may be located toward its distal end, and configured to provide a signal indicative of both a position and orientation of a portion of the catheter 10.

In an embodiment, the position detectors 18, 20, 22, may comprise electrodes (e.g., ring-type or spot type or partially masked electrodes) configured to be responsive to an electric field transmitted within the body of the subject. Such electrodes may be used to sense an impedance at a particular location and transmit a representative signal to an external computer or processor. An example of an impedance-based position detection system is the EnSite NavX™ system, commercialized by St. Jude Medical, Inc. of St. Paul, Minn., and described in U.S. Pat. No. 7,263,397, entitled "Method And Apparatus For Catheter Navigation And Location And Mapping In The Heart," which is incorporated herein by reference in its entirety.

In an embodiment, the position detectors 18, 20, 22 may comprise metallic coils located on or within the catheter 10, and may be configured to be responsive to a magnetic field transmitted through the body of the subject. Such coils may, for example, sense the strength of the field at a particular location and transmit a representative signal to an external computer or processor. An example of a magnetic-based position detection system is the Medical Positioning System (gMPS) for navigation developed by St. Jude Medical, Inc. through its MediGuide Inc. business unit of Haifa, Israel, and generally shown and described in U.S. Pat. No. 7,386,339 entitled "Medical Imaging and Navigation System," which is incorporated herein by reference in its entirety.

The ultrasound transducer 16 may be configured to project an ultrasound signal outward through adjoining tissue and/or fluid, and may further receive an ultrasound echo from such tissue or fluid. In an embodiment, the ultrasound transducer 16 may comprise a unidirectional phased array ultrasound transducer. Such a transducer may be configured to project ultrasound energy from one side of the catheter in a two dimensional plane generally aligned with the longitudinal axis of the catheter. In another embodiment, the ultrasound transducer 16 may be a radially scanning ultrasound transducer that is configured to project ultrasound energy radially outward from the catheter and may be further configured to rotate about the circumference of the catheter (e.g., through 360 degrees).

The system may additionally include a processor 24 and a display device 26. The processor, among other things, may be configured to receive position and/or orientation signals from one or more position sensors associated with the distal end portion of the catheter (e.g., position sensors 18, 20, 22), may receive ultrasound information from one or more ultrasound transducers (e.g., ultrasound transducer 16), may include and/or maintain a three-dimensional volumetric model of the cardiac anatomy, and may provide various displays to a display device 26.

Figure 2:
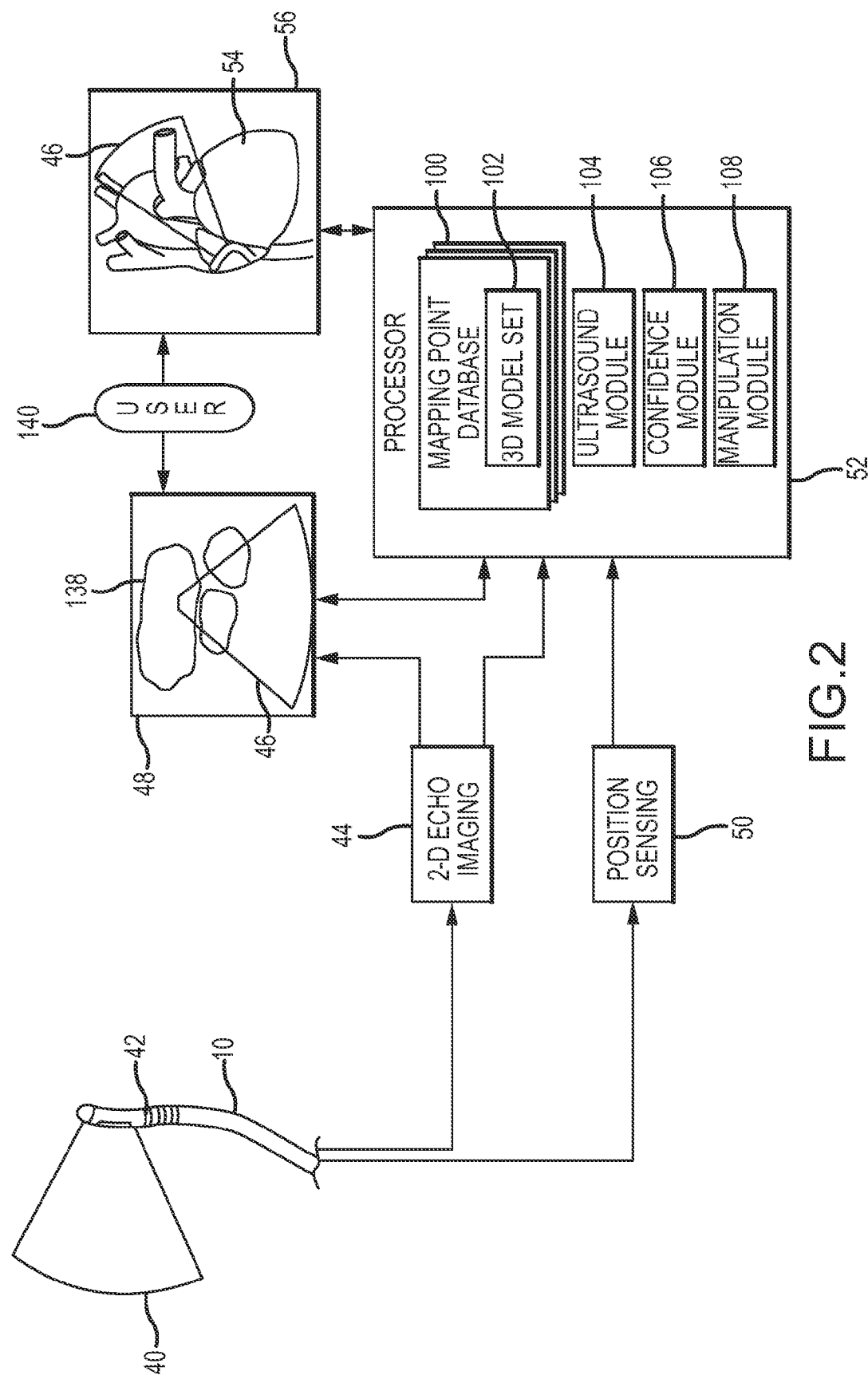
FIG. 2 is a schematic functional diagram illustrating a system for refining an anatomical model using ultrasound.

FIG. 2 generally illustrates a schematic representation of a system for refining an anatomical model. As shown, the system may include a catheter 10, such as an ICE catheter, that is capable of projecting and receiving ultrasound information 40. The ultrasound information 40 may be transmitted/received using, for example, a phased array ultrasound transducer or a radially scanning ultrasound transducer. A distal portion of the catheter 10 may further include one or more position sensors 42 that are configured to receive an external signal, from which a position and orientation may be derived. The one or more position sensors may include, for example, electrodes configured to monitor an externally generated electric field, such as with the EnSite NavX™ system, or may include magnetically responsive coils configured to monitor an externally generated magnetic field, such as with the Medical Positioning System (gMPS).

In an embodiment, the catheter 10 may provide ultrasound information 40 to a 2-D echo imaging system 44. The echo imaging system 44 may convert the received ultrasound information into an ultrasound image 46, which may be displayed on a monitor 48.

The catheter 10, may additionally provide a signal from each of one or more position sensors 42 to a position sensing system 50. From the signal, the position sensing system 50 may derive a position and orientation of the distal portion of the catheter 10. The position and orientation can have up to six degrees of freedom, depending upon the number and type of sensors and the type of system employed. In an embodiment, the derived 3D position and orientation may be provided to a processor 52 and may be logged as a mapping point, or may be used to establish or locate the ultrasound information 46 or a transducer in three dimensional space.

The processor 52 may maintain a collection of mapping points within a mapping point database 100. In an embodiment, each mapping point (P) within the mapping point database 100 may be physically defined in three dimensions (e.g., in a Cartesian space). Mapping points may be represented, for example, by an array as shown in Equation 1, where (x, y, z) represent the location of a point in three dimensions. It is noted that that an array can also include or record pitch, roll, and yaw information. Furthermore, each mapping point may comprise one or more additional parameters (e.g., ($C_1$, $C_2$, . . . , $C_n$)) that represent sensed information acquired by the catheter 10 at that particular location.

$$P=[x, y, z, C_1, C_2, \ldots, C_n] \qquad \text{Eq. 1}$$

In an embodiment, each mapping point may represent a previous location of a catheter 10, as recorded by a position sensing system 50. However, in another embodiment, the mapping points may be imported into the database from an external source, and/or may be automatically generated by the system. This collection of mapping points (i.e. the "point cloud") may provide a basis for a three-dimensional anatomical model 54 of the subject's actual cardiac anatomy 12.

In an embodiment, a three-dimensional anatomical model 54 may be constructed from the point cloud by identifying or skinning a set of the points 102 within the database 100 that are likely to represent the subject's cardiac anatomy. In a simplified and exemplary embodiment, the skin may be constructed from a plurality of shell-type elements that generally overlay or represent the outermost points of the point cloud. Other sophisticated techniques for creating such models are taught in U.S. Pat. No. 7,670,297, entitled "Chamber Mapping System;" U.S. Pat. No. 7,263,397, entitled "Method and Apparatus for Catheter Navigation and Location and Mapping in the Heart," and in U.S. Patent Publication No. 2008-0221643 (application Ser. No. 11/715,919), entitled "System and Method for Correction of Inhomogeneous Fields," which are all herein incorporated by reference in their entirety. Once a shell model has been constructed from the collection of mapping points 100, the processor 52 may display a representation of the model 54 on a model display 56.

As further illustrated in FIG. 2, the processor 52 may include an Ultrasound Module 104 that is configured to receive a representation of the ultrasound echo image 46 and relate the representation to the collection of mapping points. The processor 52 may also include a Confidence Module 106 that may determine a relative measure of "confidence" or "trustworthiness" for each mapping point. In an embodiment, this measure of confidence may be based on the amount of corroborating information provided by an ultrasound image, and may be used to provide a measure of certainty as to whether a recorded mapping point lies on a tissue boundary. Furthermore, the processor 52 may include a Manipulation Module 108 that may alter a visual attribute of a displayed mapping point based on a measure of confidence, and/or may automatically manipulate the shelled model to only include mapping points with a certain minimum measure of confidence. For purposes of this description, each functional "module" has been illustrated separately from the other modules, however, this should not be interpreted to reflect or require a particular software configuration or organization. Furthermore, it is contemplated that there may be overlap or dependencies between the various modules when implemented. Each module will be described is greater detail below.

Figure 3:
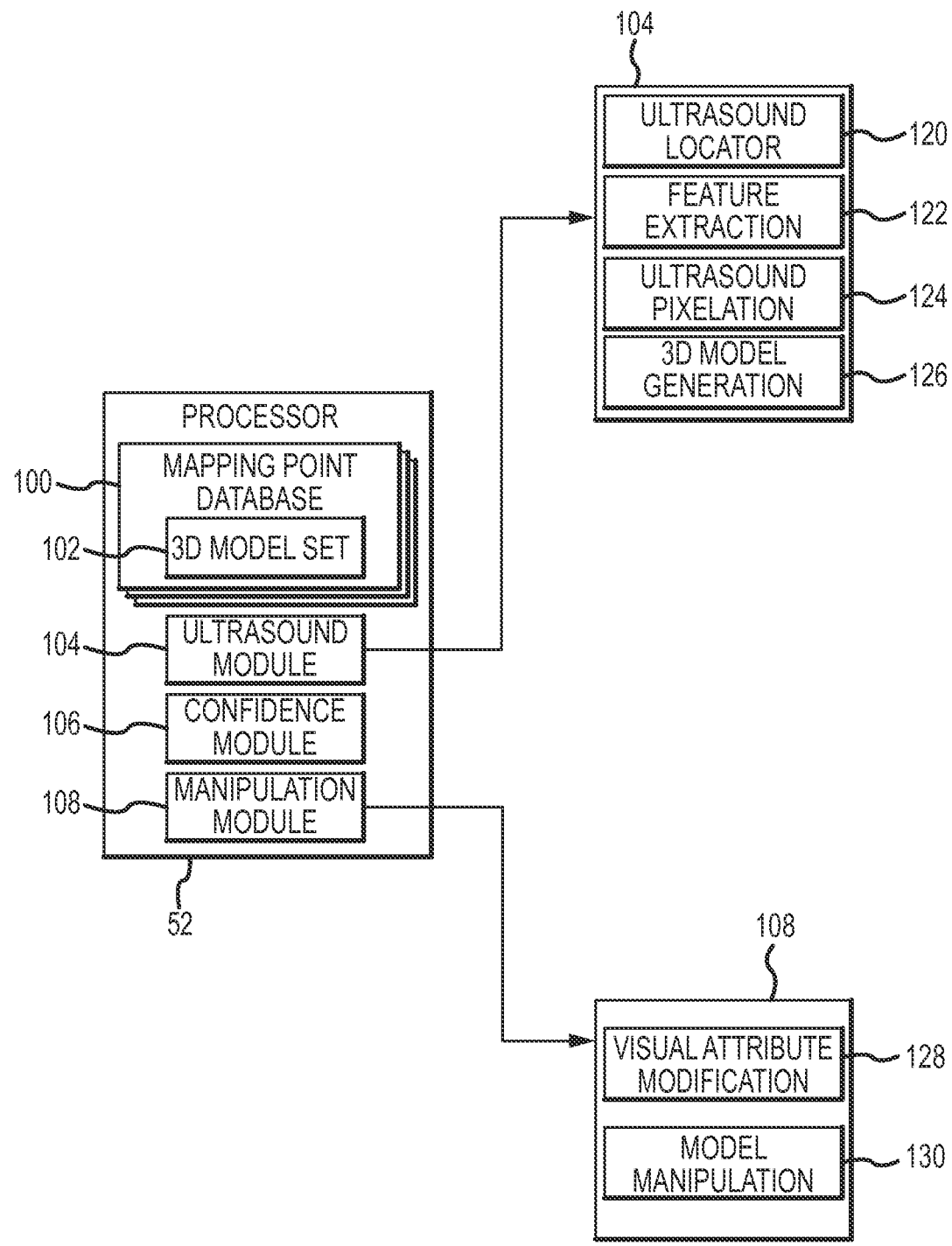
FIG. 3 is a further functional representation of features associated with a processor such as shown in FIG. 2.

FIG. 3 is a further refined diagrammatic illustration of various modules of an embodiment of a processor, such as the processor 52 generally illustrated in FIG. 2. As shown, the ultrasound module 104 and manipulation module 106 may each include one or more sub-modules or sub-functions. In an embodiment, the Ultrasound Module 104 may include an Ultrasound Locator sub-module 120 that is configured to locate two-dimensional ultrasound information 40 within 3D model space.

Figure 4:
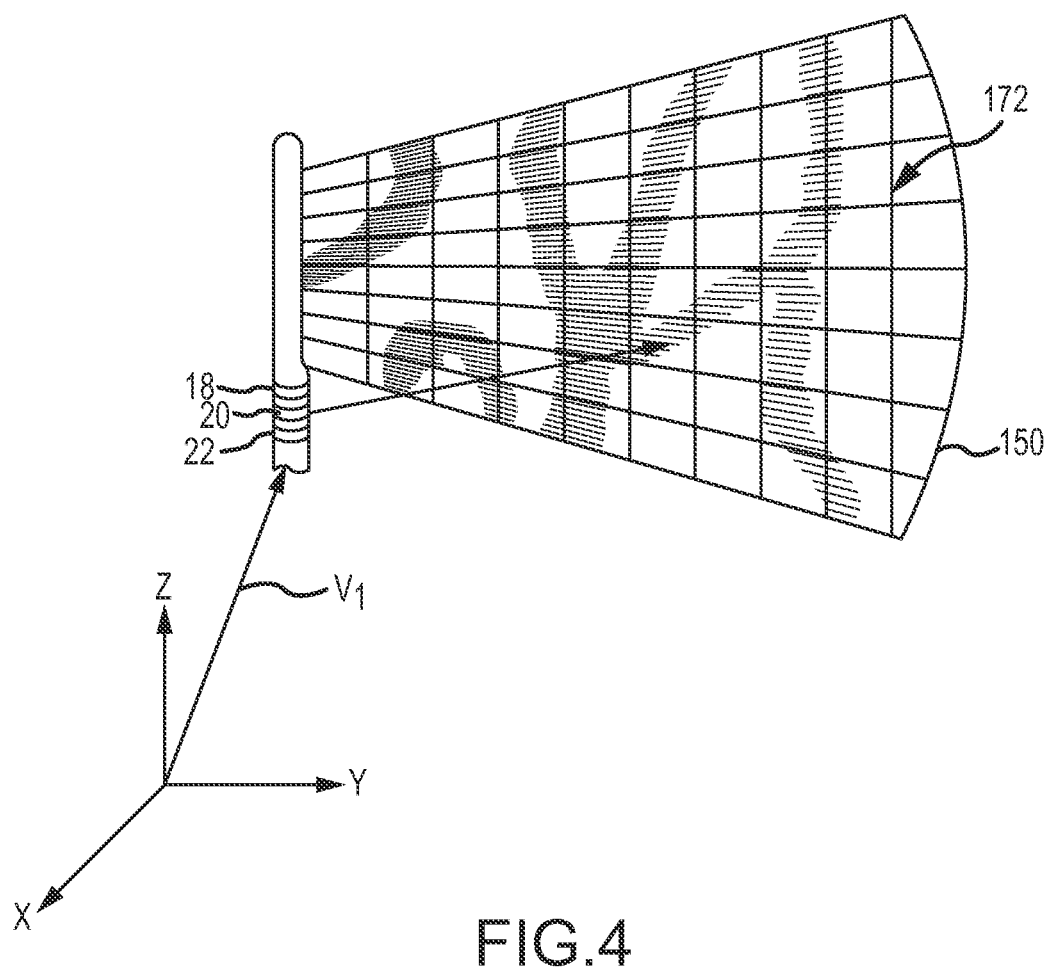
FIG. 4 is an illustration of a catheter projecting ultrasound.

As generally illustrated in FIG. 4, the Ultrasound Locator module 120 may use the position and orientation of the catheter ($V_1$) (as provided by a positioning system 50), together with a knowledge of the physical relationship between position sensors (e.g., sensors 18, 20, 22) and the ultrasound spread 150, to locate the ultrasound 150 in three dimensional model space. After the two-dimensional ultrasound information 150 is located within the model space, the processor 52 may display it together with the three-dimensional anatomical model 54 and any associated mapping points, as generally shown in FIG. 5a.

Referring again to FIG. 3, the Ultrasound Module 104 may further include a Feature Extraction sub-module 122 that may use a sensed position and orientation of the ultrasound information 150 to extract features from the three-dimensional anatomical model 54 that lie within a given tolerance of the 2D ultrasound plane. This concept is generally illustrated with general reference to FIGS. 5a and 5b.

The Extraction sub-module 122 may generally define a 2D model slice plane that exists within the 3D model space and contains ultrasound information 150. This slice plane may be used as a cutting plane for the purpose of extracting features from the model. In an embodiment, the intersection of the model slice plane and cardiac model 54 may create a set of boundary lines that represent the walls of a cardiac anatomy within that plane. As shown generally in FIGS. 5b, once extracted, the boundary information 152 may then be overlaid on an independent visualization of the ultrasound information 154 to create an augmented echo image 156 Likewise, mapping points that exist within a given tolerance of the model slice plane may be extracted and, if desired, displayed within the augmented echo image 154.

Figure 5A:
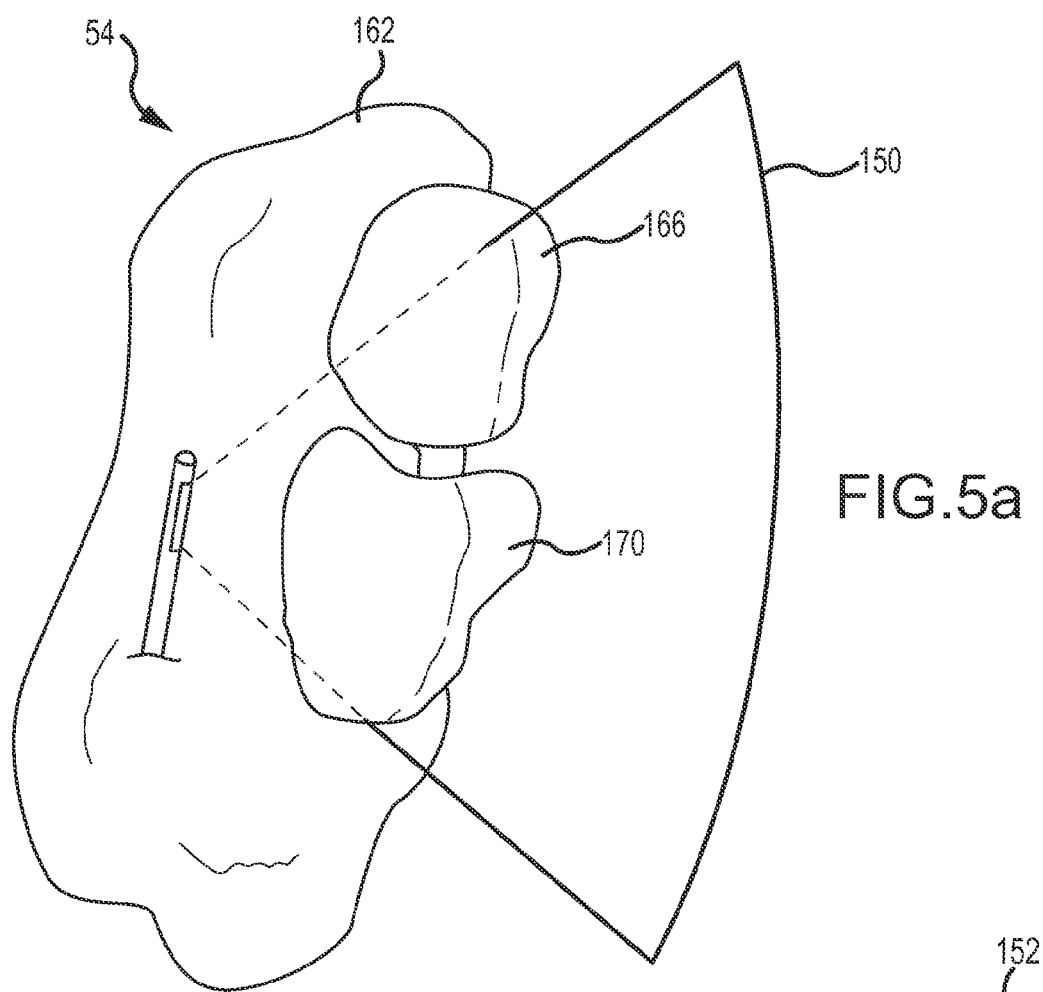
FIG. 5a is a general representation of a volumetric cardiac model including a representation of a phased array catheter.
Figure 5B:
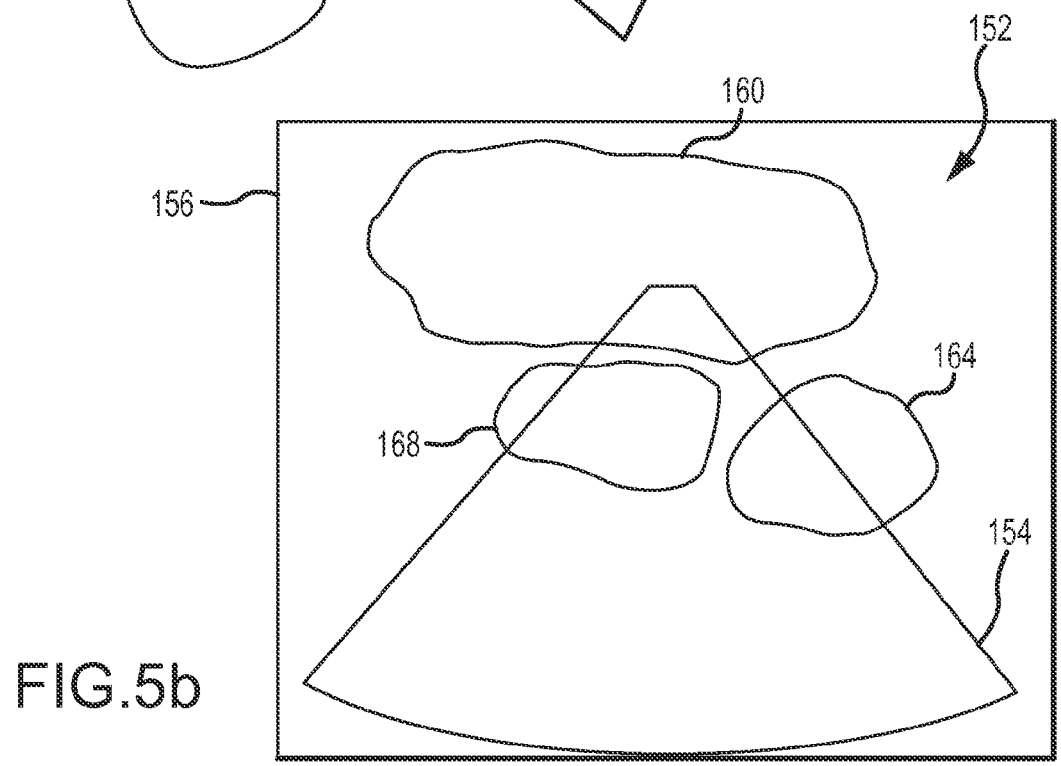
FIG. 5b is a general representation of an augmented echo image including a phased array ultrasound image and including boundary information.

In the exemplary illustration shown in FIGS. 5a and 5b, the augmented echo image 156 may contain a first boundary marker 160 that corresponds to structure 162 depicted in FIG. 5a Likewise a second boundary marker 164 may correspond to structure 166, and a third boundary marker 168 may correspond to structure 170.

The Ultrasound Module 104 may further include an Ultrasound Pixelation sub-module 124 that may analyze a visualization of the ultrasound information 150, deconstruct it into a plurality of pixels, and assign each pixel a representative image intensity corresponding to sensed ultrasound reflectivity. FIG. 4 illustrates an exemplary pixel subdivision, where the ultrasound spread has been initially divided into a plurality of regularly shaped pixels (e.g., pixel 172). In practice, a pixel resolution may be on the order of 320 to 640 pixels per inch; however, the density may be more or less depending on the speed and memory constraints of the processor 52. Once the image has been subdivided into the plurality of image pixels, each pixel may then be assigned an intensity value corresponding to the average perceived image intensity across that pixel. In an embodiment, the intensity value for each pixel may be a numeric value.

Figure 6:
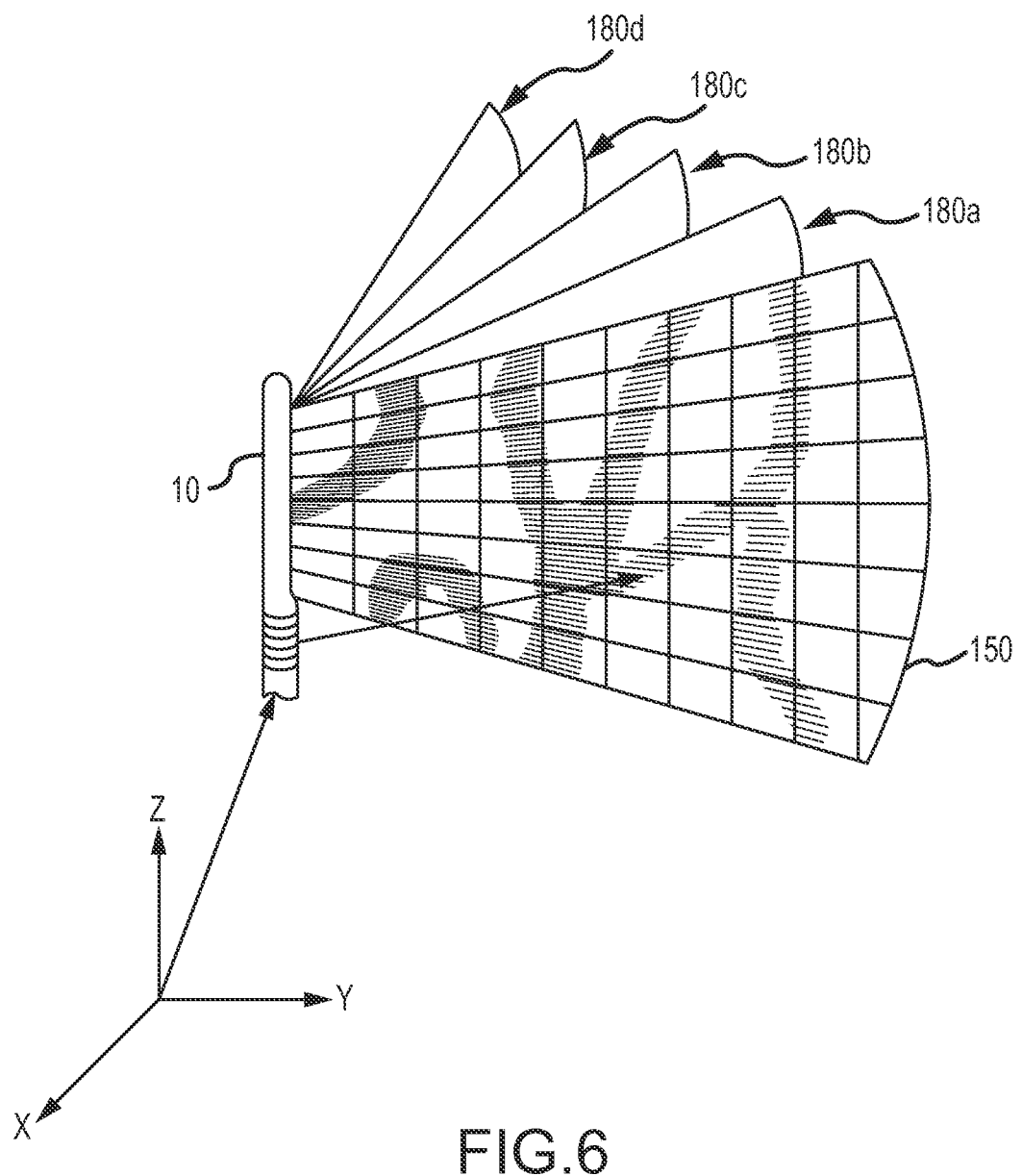
FIG. 6 is an illustration of a catheter such as shown in FIG. 4, generally demonstrating ultrasound being swept around a longitudinal axis of the catheter.

Finally, the Ultrasound Module 104 may include a 3D Model Generator 126. As shown in FIG. 6, during a procedure, the catheter 10 may be manipulated in a manner that causes the ultrasound spread 150 to take a plurality of different positions and orientations. For example, simply rotating the catheter may cause the ultrasound spread 150 to assume poses 180a, 180b, 180c, 180d. Similarly, the catheter may be translated, or deflected away from its longitudinal axis to further manipulate the ultrasound.

Figure 7:
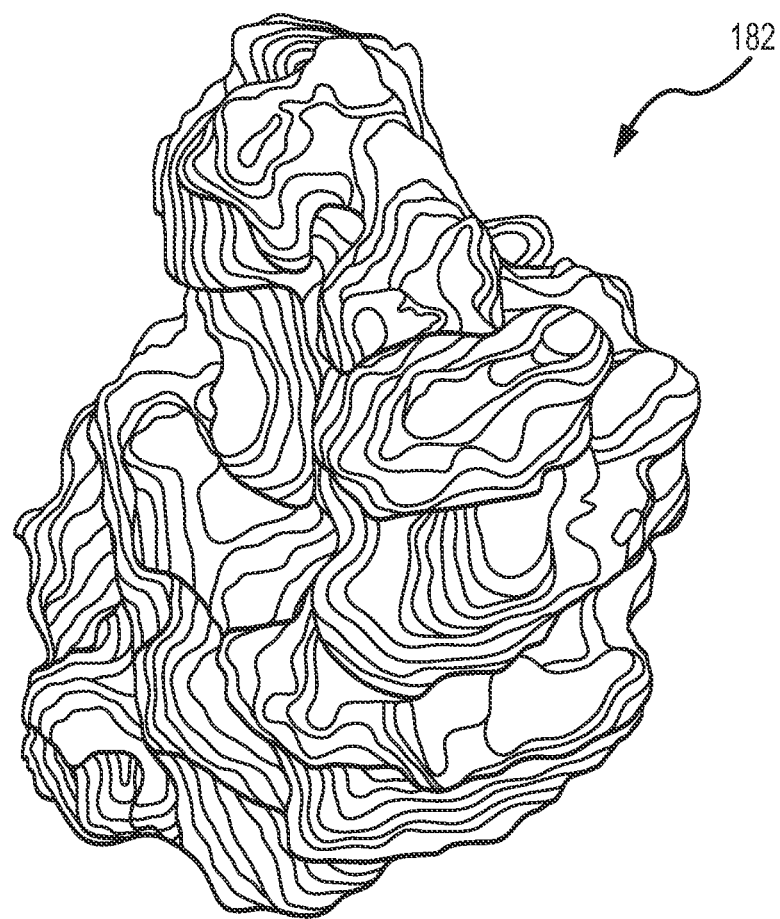
FIG. 7 is an illustration of a voxel model of a chamber of a subject's cardiac anatomy.

At each pose, pixels within the visualization may be spatially located in three-dimensional space. Knowing these locations, the Model Generator 126 may then map associated pixel intensities to corresponding positions within a three-dimensional volume. Each intensity within the 3D space may be represented as a volumetric pixel (voxel), such as a cubic element, that has a corresponding intensity. This mapping may then result in a three-dimensional intensity map that is assembled from the various slice data. As successive ultrasound poses are recorded and associated to the 3D space, the model may be successively updated, for example, by using a Bayesian Inference Algorithm. By setting or providing an appropriate intensity threshold, the Model Generator 126 may effectively "hide" portions of the volume that exhibit an ultrasound reflection intensity below the threshold. As illustrated in FIG. 7, the resulting unhidden portion of the volume may be viewed as a voxel model 182 that represents a cardiac structure (or other objects exhibiting a comparatively high ultrasound reflectivity (e.g., foreign objects)).

Referring again to FIG. 3, the processor 52 may include a Confidence Module 106 that may determine a relative measure of "confidence" or "trustworthiness" for each mapping point within the mapping point database 100. In an embodiment, the measure of confidence or trustworthiness may be greater for mapping points that are confirmed to be immediately adjacent an actual tissue boundary, and lesser for mapping points that are more interior to the chamber.

Figure 8:
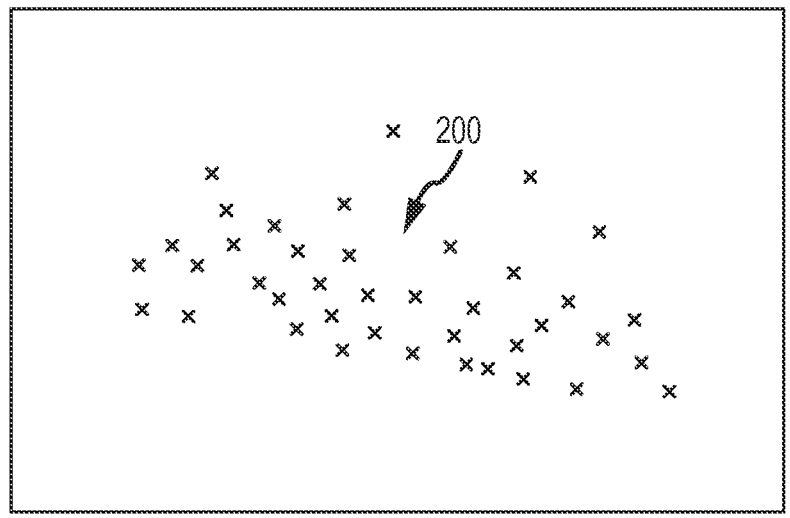
FIG. 8 is a two-dimensional subset of a mapping point cloud.

FIG. 8 illustrates an exemplary portion of a mapping point cloud 200. As generally described above, each mapping point, represented by an "x" is registered in the mapping point database 100 as a three-dimensional location. The illustrated mapping points 200 represent an extracted subset of points from the database that may lie in, or may be proximate to a two-dimensional plane. Without further evidence, each displayed mapping point may be substantially similar to all other displayed mapping points. In an embodiment, the Confidence Module 106 may examine each mapping point in light of other available information or evidence to aid the system in determining which points are more likely to represent a tissue boundary. An example of evidence that may be used to provide a measure of confidence may be the ultrasound information obtained from an intracardiac echo catheter.

Figure 9:
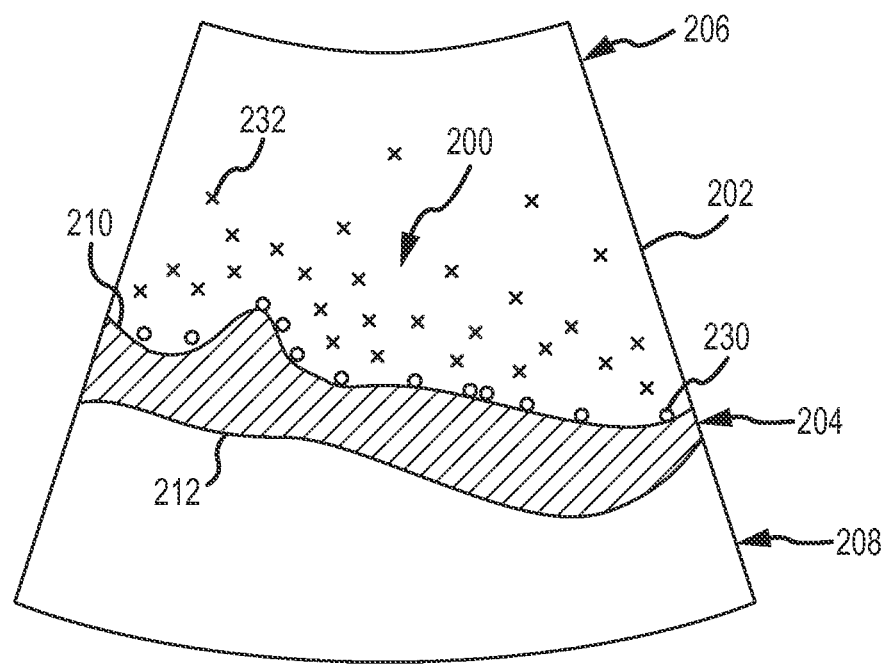
FIG. 9 illustrates the mapping points of FIG. 8, generally overlaid on an ultrasound image.

As shown in FIG. 9, a planar collection of mapping points, such as illustrated in FIG. 8, may be overlaid on an ultrasound image 202 captured from the same spatial plane as the points 200. Prior to a confidence evaluation, the ultrasound image 202 may be pixilated using known or herein described methods. In an embodiment, the Confidence Module 106 may analyze the pixilated ultrasound image to determine an intensity gradient over the image. This analysis may involve numerical methods, such as, for example, by calculating the difference in intensity values between adjacent pixels or groups of pixels. The existence of a gradient that is above (or below) a given threshold may signify a transition between fluid or tissue with a low ultrasound reflectivity and fluid or tissue with a higher reflectivity. Such a transition may detect boundaries between blood (i.e., lower reflectivity) and cardiac tissue (i.e., higher reflectivity). For example, within the exemplary ultrasound image 202 illustrated in FIG. 9, there may be one or more areas of high ultrasound reflectivity 204 that may represent a portion of the cardiac wall. Adjacent these high-intensity areas, there may be areas of lesser intensity (e.g. areas 206, 208) that may represent cavities in or near the cardiac anatomy 204. For example, region 206 may represent an area inside the cardiac chamber, and area 208 may represent an area outside the cardiac chamber. The intensity gradient would likely be the highest at the transitions between area 204 and areas 206, 208 (i.e., respectively, at boundaries 210, 212)

Once tissue boundaries have been identified, a measure of confidence may be assigned to each mapping point based on its proximity to the boundary. In an embodiment, the confidence value may be based on a point's absolute proximity to the boundary. For example, mapping points more proximate to the perceived tissue boundary may be assigned a higher confidence value than points more distal to the boundary. While FIG. 9 illustrates an overlay of mapping points on the ultrasound in a two-dimensional construct, the mapping point overlay and/or assignment of confidence values may likewise be performed in three dimensions, such as with an ultrasound model as generally shown in FIG. 7.

The Confidence Module 106 may additionally be capable of identifying anomalies or abnormalities in an ultrasound image by examining the magnitude of the ultrasound intensity. In an embodiment, if an abnormality is detected, the Confidence Module 106 may lower the corresponding confidence of proximate mapping points. For example, a high-intensity plateau in the intensity map, may indicate the presence of a metallic object that is reverberating. Similarly, a low-intensity plateau in the intensity map may indicate a highly echogenic object that does not transmit sound deeper. In either circumstance, the system may decrease the confidence of any points immediately proximate the plateau, such as for points that may lie in ultrasound darkness due to a object.

Finally, referring again to FIG. 3, the Manipulation Module 108 may include a Visual Attribute Modification Module 128 that may modify one or more visual attributes of overlaid mapping points based on an associated degree of confidence. Additionally, Manipulation Module 108 may include a Model Manipulation Module 130, that may directly manipulate the skinned model based on the various confidence measures.

As illustrated in FIG. 9, the processor 52 may alter the appearance of one or more mapping points 200 based on a mapping point's confidence value. In an embodiment, the processor may use symbols to represent each mapping point, where the symbol is chosen to represent, for example, a range of confidence values. In an exemplary embodiment, the system may display mapping points with a confidence value above a particular threshold (i.e. an upper range) as an "o" (e.g., mapping point 230). Likewise, mapping points having a confidence value below the threshold may be displayed as an "x" (e.g., mapping point 232). In another embodiment, the processor 52 may display each mapping point using a color that may be selected from a spectrum corresponding to a range of confidence values. As may be appreciated, various other designators or identifiers may be used to provide an indication of the confidence value assigned to a mapping point.

Figure 10A:
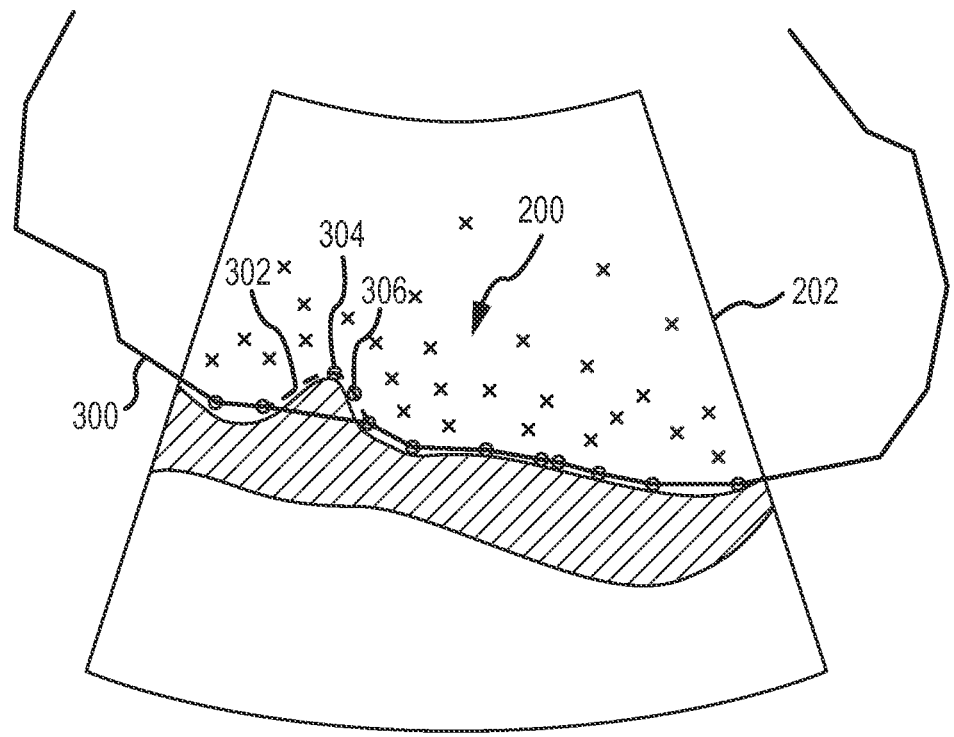
FIG. 10a is the illustration of FIG. 9, with model boundary information generally included
Figure 10B:
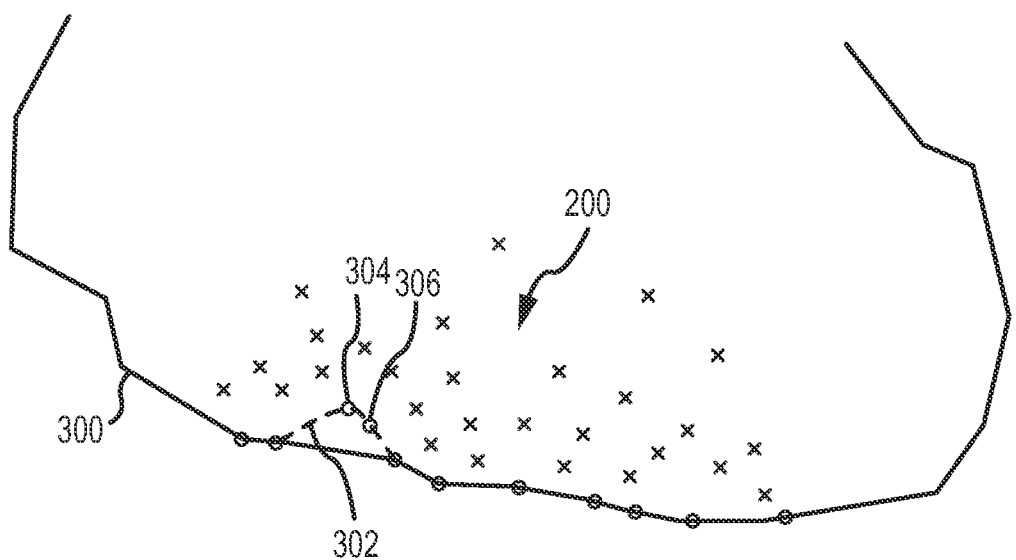
FIG. 10b is the illustration of FIG. 10a with the ultrasound image removed.

The Manipulation Module 108 may also be capable of manipulating a skinned model to include mapping points that have been assigned a sufficiently high confidence value. Similarly, if a given model set 102 includes mapping points that do not meet a particular confidence threshold, the system may exclude them from the model. In an exemplary embodiment, as shown in FIGS. 10a and 10b, an existing model 300 can be constructed by skinning the outermost points of the point cloud (note that mapping points outside of the ultrasound image 202 are not illustrated). The augmented ultrasound image in FIG. 10a illustrates that the model 300 that bisects a portion of the cardiac tissue, and is therefore inaccurate. Following the confidence evaluation, a corrected model 302 may be generated that specifically incorporates more interior mapping points 304 and 306. FIG. 10b illustrates the model 300 and corrected model 302 without the visual benefit of the ultrasound image 200.

In an embodiment, the Model Manipulation Module 130 may be configured to automatically adjust the 3D Model Set 102 (and corresponding skinned model) based on the mapping point confidence evaluation. In another embodiment, the system may present a visualization of the augmented ultrasound image to a user (similar to FIG. 9 or 10a), and allow the user to manually adjust the model 300 at his/her discretion. In an embodiment, if a change is made to the model set 102 in one two-dimensional plane, the manipulation module 130 may be configured to make any necessary adjustments in adjacent planes to ensure the three dimensional continuity of the model surface.

Figure 11:
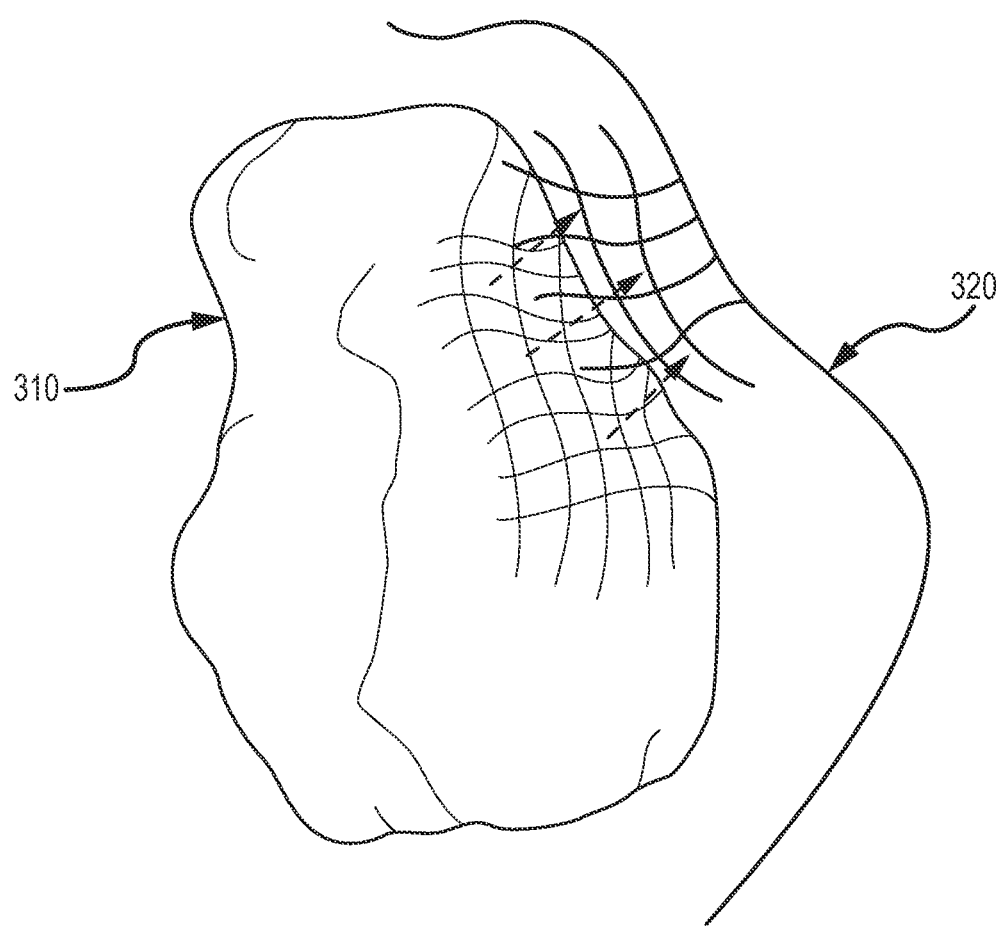
FIG. 11 is a general illustration of a skinned model adjusted in three-dimensional space in view of a voxel-based ultrasound model.

While FIGS. 10a and 10b illustrate the model correction in a two-dimensional context, as generally illustrated in FIG. 11, the correction may also be performed in three dimensions. In an embodiment, prior to a confidence evaluation, a three-dimensional mapping point (e.g., NavX) model 310 may be globally scaled, rotated, and/or translated to best align with a three-dimensional ultrasound model 320 (of the type illustrated in FIG. 7). Once a best fit is obtained, the adjusted model set, along with interior mapping points, may be evaluated to determine the degree of confidence for each point. The Model Manipulation Module 130 may then include or eliminate mapping points from the Model Set 102 based on their corresponding confidence value.

Figure 12A:
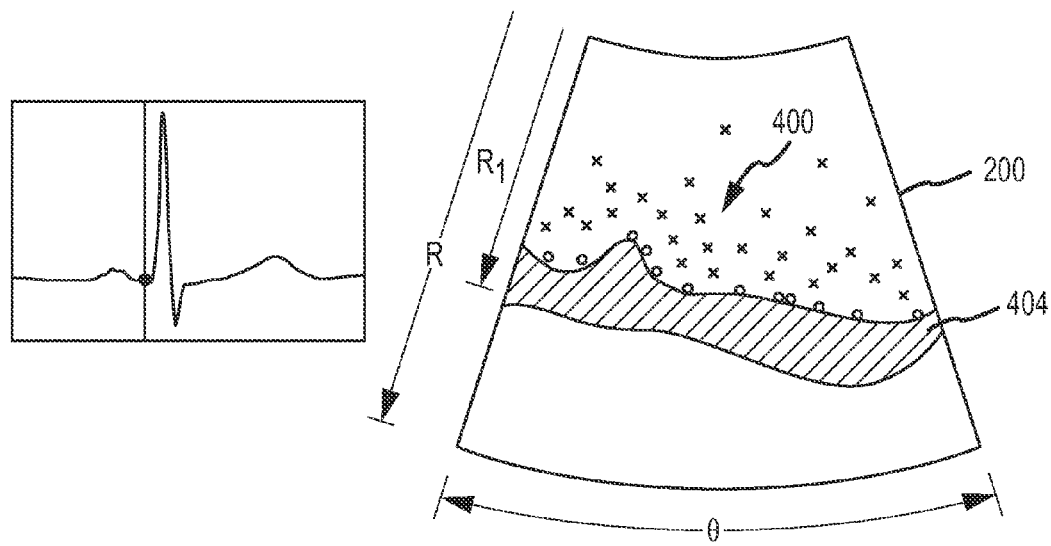
FIG. 12a is a general illustration of an ultrasound image and overlaid mapping point cloud keyed to a first phase of an anatomical rhythm.
Figure 12B:
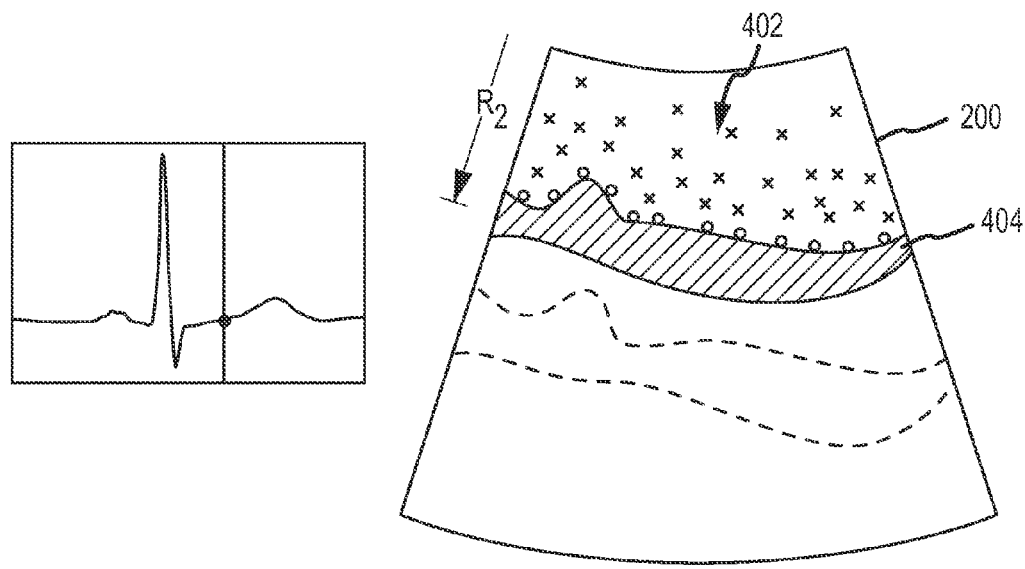
FIG. 12b is a general illustration of an ultrasound image and overlaid mapping point cloud keyed to a second phase of an anatomical rhythm.

In an embodiment, the mapping points may be discretely recorded and/or adjusted to account for one or more external factors, such as, for example, cardiac rhythm or patient breathing. For periodically occurring events, such as the cardiac cycle, the mapping point cloud may be a function of, or correlated to account for these factors. For instance, timing signals can be filtered and/or matched to images taken at corresponding signals/timings. In an embodiment, each mapping point may include additional parameters that indicate the conditions under which the point was recorded. Multiple mapping point clouds may then be assembled by grouping points together that were recorded under similar conditions. By monitoring the same or related factors during the real-time procedure, the system may choose the point cloud that most closely resembles the current conditions (e.g., using a lookup table). For example, FIGS. 12a and 12b represent two mapping point clouds 400, 402 that were recorded at different points within the sinus rhythm. As shown in the two figures, the ultrasound image illustrates that the cardiac tissue 404 has moved from a first position $R_1$ to a second, more contracted position $R_2$. By monitoring the subject's current electrocardiogram, they system may choose and/or modify the point cloud to more accurately reflect the current conditions of the heart, and may help to avoid erroneously overlaying mapping points. In an embodiment, compensation algorithms may be used to interpolate between various point clouds.

In an embodiment where the point cloud is a function of external factors, if desired the confidence evaluation and model adjustment may be performed on each distinct mapping point subset, such as shown in FIGS. 12a and 12b. In an embodiment, if the model is manipulated at one point in the cardiac phase, the system may extrapolate the modification to model sets at previous and/or subsequent times within the rhythm.

In an embodiment, the system may further evaluate the model to determine a "degree of influence" for each point along the model. In this manner, points that possess a high degree of negative influence may be identified, deleted, and/or morphed, for example, to a more neutral position. Alternatively, points exhibiting a highly positive degree of influence may be identified and preserved.

Figure 13:
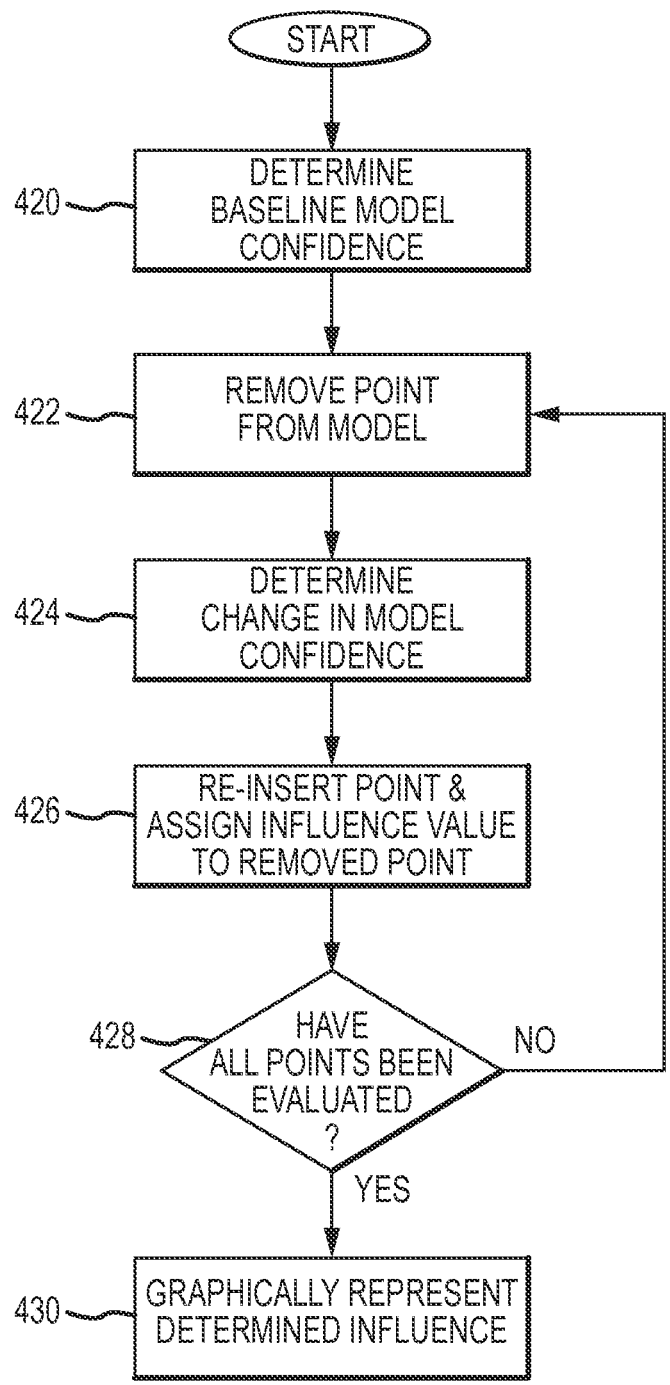
FIG. 13 is a flow diagram illustrating a method for determining a degree of influence for a model.
Figure 14:
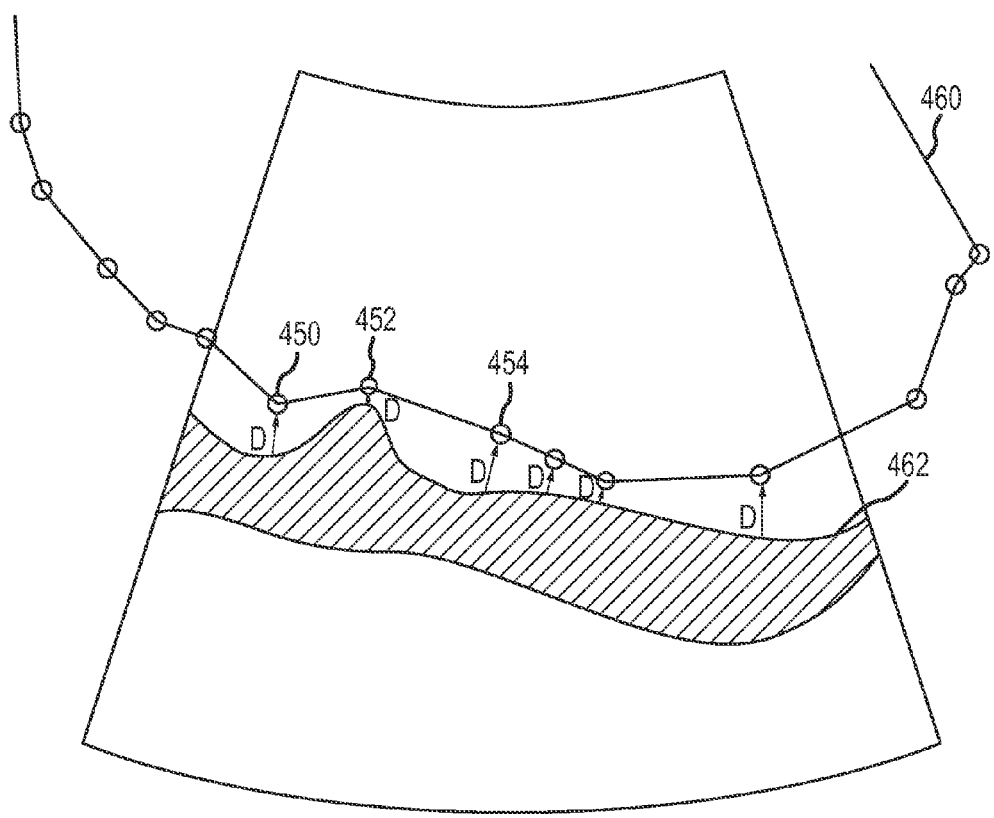
FIG. 14 is a general representation of an augmented echo image and an illustration of a process for determining a model confidence.

FIG. 13 generally illustrates an example of a method for determining and/or displaying a degree of influence for each point (or certain relevant points) within the model. In an embodiment, the system may first determine a baseline model confidence 420. FIG. 14 generally illustrates an exemplary approach for computing a model confidence. In an embodiment, the system may first identify points (e.g., points 450, 452, 454) along the surface of the model 460. Analytically, a distance (e.g., distance D) may be computed between each model point and the displayed ultrasound edge boundary 462. These distances may be used (e.g., summed) to compute a single confidence value. This value may serve as the baseline for computing the model influence attributable to each point.

Referring again to FIG. 13, once a baseline model confidence value is established (step 420), the system may then temporarily hide one or more points from the set (step 422), and re-build the model from the remaining points. Using the augmented model, the system may then compute a new confidence value, and compare it with the baseline value to determine how the hidden point influences model accuracy (step 424). The hidden point may be reinserted into the model and associated with its measure of influence (change in confidence from the baseline) (step 426). This process may repeat until all of the relevant points have been evaluated (step 428). Finally, the model may be altered to visually discriminate points or areas of higher relative influence from points or areas of lower influence (step 430). For example, the model may be colored or shaded to reflect different levels of influence. Alternatively, varying symbols or labels may be applied to the points or areas to reflect the varying levels of influence.

In the above-described embodiments, registration may be performed using the position and orientation signals received from the catheter positioning system; however refinements to this gross positioning may also be employed. In an embodiment, the system may use an iterative closest point ("ICP") registration algorithm to align the model boundaries with the ultrasound information. While an ICP registration may occur in three dimensions, a less computationally heavy method may involve performing a plurality two-dimensional registrations at varying angles to each other.

In an embodiment employing a registration algorithm to further align or correlate the model and the captured ultrasound, the system may process or optimize the rotation, translation, and/or scaling of one image to more accurately match the other. Such an algorithm or routine may for example, facilitate the minimization of a least-squares deviation between the models, by using slight perturbations to the model while observing the resultant alignment. In an embodiment, this may result in an "optimal registration" being a local minima, where any perturbation results in a less-optimal alignment. In an embodiment, however, the system may further explore the model registration space for the existence of multiple local minima. If multiple correlations or fits exist and are identified, the system may be configured to present each potential solution/alignment to the user in turn, and allow the user to select which one to use.

In a further embodiment, the system may analyze the spatial distribution of the vector error between the model and ultrasound boundaries. This analysis may be performed, for instance, to gain a more complete understanding of existing translation, rotation, and/or scaling errors/offsets. For example, as generally illustrated in FIG. 14, if translation error dominates, most or all error vectors will be in a uniform direction and include at least a minimum magnitude. If, however, rotation error dominates, the vector error close to the transducer may be negligible, however, it may linearly increase with the distance away from the transducer.

While numerous embodiments of this disclosure have been described above with a certain degree of particularity, those skilled in the art could make numerous alterations to the disclosed embodiments without departing from the spirit or scope of the invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed:

1. A method of refining a model comprising:
acquiring a two-dimensional echocardiogram from a catheter located within a subject;
acquiring, from a plurality of position detectors associated with a distal portion of the catheter, a position and orientation of the catheter associated with the acquired two-dimensional echocardiogram;
acquiring a three-dimensional anatomical model from the subject, the three dimensional model including one or more mapping points within a three dimensional model space; and
using a processor to:
relate the two-dimensional echocardiogram and the associated position and orientation of the catheter to the one or more mapping points of the three-dimensional anatomical model;
determine a degree of influence value for the one or more mapping points;
display the one or more mapping points with a visual attribute that corresponds to the determined degree of influence value; and refine the three-dimensional anatomical model based on the visual attribute;
wherein using the processor to determine a degree of influence value for the one or more mapping points includes:
determining a confidence value for the model;
removing at least one of the one or more mapping points from the model; and
calculating a change in the confidence value of the model attributable to the at least one removed point.

2. The method of claim 1, wherein the visual attribute is a color selected from a spectrum of colors, the selected color representing a range of influence values.

3. The method of claim 1, wherein the visual attribute is a symbol that represents a range of influence values.

4. The method of claim 1, wherein determining a confidence value for the model includes:
identifying a boundary from the two-dimensional echocardiogram;
calculating a distance between each of the one or more mapping points of the model and the identified boundary.

5. The method of claim 4, further comprising aggregating the respective distances.

6. The method of claim 1, wherein the two-dimensional echocardiogram is acquired from an ultrasound transducer associated with the distal portion of the catheter.

7. The method of claim 6, wherein using the processor to relate the two-dimensional echocardiogram and the associated position and orientation of the catheter to the one or more mapping points of the three-dimensional anatomical model includes:
receiving an indication of the position and orientation of the ultrasound transducer; and
registering the two-dimensional echocardiogram within the three-dimensional model space using the position and orientation of the ultrasound transducer.

8. The method of claim 7, wherein using the processor to relate the two-dimensional echocardiogram and the associated position and orientation of the catheter to the one or more mapping points of the three-dimensional anatomical model further includes refining the registration using an iterative closest point registration algorithm.

9. The method of claim 7, wherein the indication of the position and orientation of the ultrasound transducer is received from the plurality of position detectors associated with the distal portion of the catheter.

10. The method of claim 7, further comprising displaying a representation of the two dimensional echocardiogram within the three-dimensional model space.

11. A system for refining a three-dimensional anatomical model, the system comprising:
a processor having stored therein a database comprising a three-dimensional anatomical model from a subject including one or more mapping points existing in a three-dimensional model space;
an ultrasound echo imaging system including a catheter configured to acquire a two-dimensional echocardiogram from the subject; and
a plurality of position detectors configured to determine a position and orientation of the catheter associated with the two-dimensional echocardiogram;
wherein the processor is configured to do the following:
relate the two-dimensional echocardiogram and the position and orientation of the catheter associated with the two-dimensional echocardiogram to the one or more mapping points;
determine a degree of influence value for the one or more mapping points;
display the one or more mapping points with a visual attribute that corresponds to the determined degree of influence value; and
refine the three-dimensional model based on the visual attribute; and
wherein the processor is further configured to:
determine a confidence value for the model;
remove at least one of the one or more mapping points from the model; and
calculate a change in the confidence value of the model attributable to the at least one removed point.

12. The system of claim 11, wherein the visual attribute is a color selected from a spectrum that corresponds to a range of influence values.

13. The system of claim 11, wherein the visual attribute is a symbol that represents a range of influence values.

14. The system of claim 11, wherein the processor is further configured to:
identify a boundary from the two-dimensional echocardiogram;
calculate a distance between each of the one or more mapping points of the model and the identified boundary; and
aggregate the respective distances.

15. The system of claim 11, wherein the processor is further configured to evaluate a spatial distribution of a vector error between the model and an ultrasound boundary.

16. A system for assessing the accuracy of an anatomical model, the system comprising:
a processor having stored therein a database comprising a three-dimensional anatomical model from a subject including one or more mapping points existing in a three-dimensional model space;
an ultrasound echo imaging system configured to acquire a two-dimensional echocardiogram from the subject from an intracardiac echo catheter, the intracardiac echo catheter including a plurality of position detectors configured to determine a position and orientation of the catheter associated with the two-dimensional echocardiogram;
wherein the processor is configured to do the following:
relate the two-dimensional echocardiogram and the position and orientation of the catheter to the one or more mapping points;
determine a degree of influence value for the one or more mapping points;
display the one or more mapping points with a visual attribute that corresponds to the determined degree of influence value; and
refine the three-dimensional anatomical model based on the visual attribute; and
wherein the processor is further configured to:
determine a confidence value for the model;
remove at least one of the one or more mapping points from the model; and
calculate a change in the confidence value of the model attributable to the removed point.

* * * * *